US005559893A

United States Patent [19]

Krokstad et al.

[11] Patent Number: 5,559,893

[45] Date of Patent: Sep. 24, 1996

[54] METHOD AND DEVICE FOR ACTIVE NOISE REDUCTION IN A LOCAL AREA

[75] Inventors: Asbjørn Krokstad; Odd K. Ø. Pettersen; Svein Sørsdal, all of Trondheim, Norway

[73] Assignee: Sinvent A/S, Trondheim, Norway

[21] Appl. No.: 374,578

[22] PCT Filed: Jul. 9, 1993

[86] PCT No.: PCT/NO93/00114

§ 371 Date: Mar. 21, 1995

§ 102(e) Date: Mar. 21, 1995

[87] PCT Pub. No.: WO94/02935

PCT Pub. Date: Feb. 3, 1994

[30] Foreign Application Priority Data

Jul. 22, 1992 [NO] Norway .................................... 922911

[51] Int. Cl.[6] ............................ A61F 11/06; H03B 29/00; H04R 27/00

[52] U.S. Cl. ................................ 381/71; 381/94; 381/83; 381/93; 381/73.1

[58] Field of Search ................................ 381/71, 94, 72, 381/73.1, 86, 83, 93

[56] References Cited

U.S. PATENT DOCUMENTS

| | | | |
|---|---|---|---|
| 4,489,441 | 12/1984 | Chaplin | 381/71 |
| 4,977,600 | 12/1990 | Ziegler | 381/72 |
| 5,003,606 | 3/1991 | Bordewijk | 381/93 |
| 5,133,017 | 7/1992 | Cain et al. | 381/71 |
| 5,193,117 | 3/1993 | Ono et al. | 381/71 |
| 5,400,409 | 3/1995 | Linhard | 381/94 |

FOREIGN PATENT DOCUMENTS

| | | | |
|---|---|---|---|
| 0405331 | 2/1991 | European Pat. Off. . | |
| 9205538 | 2/1992 | WIPO . | |
| WO94/29846 | 12/1994 | WIPO | 381/71 |
| WO94/29845 | 12/1994 | WIPO | 381/71 |

*Primary Examiner*—Curtis Kuntz
*Assistant Examiner*—Xu Mei
*Attorney, Agent, or Firm*—Jacobson, Price, Holman & Stern, PLLC

[57] ABSTRACT

A method for active noise reduction based on destructive interference of sound waves in order to reduce the energy in a sound field employs two omnidirectional microphones (M1, M2) provided in connection with a loudspeaker. The acoustic feedback of the microphones is eliminated by a closed loop consisting of the microphones and the loudspeaker. The loudspeaker used is an open loudspeaker with a dipole characteristic, thus causing one of the microphones to be more sensitive to the far field and thereby to the noise which has to be suppressed. The method is implemented by a device which comprises a digital signal processor (DSP) for processing the microphone signals and which transmits an output signal to the loudspeaker where the feedback component from the loudspeaker is substantially eliminated, while the output signal's phase and amplitude are adjusted in such a manner that an effective cancellation of the noise is obtained in an area around the loudspeaker's near field. The DSP can preferably be implemented in the form of software modules on an integrated circuit. With the method and the device an integrated reduction in noise level of almost 20 dB is achieved depending on how the filtering in the DSP is adapted. In practice a quiet zone can be obtained in the loudspeaker's near field with an attenuation band which extends from approximately 100–500 Hz.

14 Claims, 1 Drawing Sheet

METHOD AND DEVICE FOR ACTIVE NOISE REDUCTION IN A LOCAL AREA

The invention concerns a method for active noise reduction in a local area in accordance with the introduction of claim 1. The invention also concerns a device for active noise reduction in a local area in accordance with the introduction of claim 9.

There is a known method of using an active noise reduction based on sound waves destructive interference in order thereby to reduce the energy in a sound field. A so-called cancelling sound source is used for producing a sound field with the same spectrum as the sound field which is to be suppressed, but opposite in phase thereto. When the amplitude of the two sound fields is identical, the result will ideally be a total suppression of the sound energy by phasing it out. The problem is to find the cancelling sound field which provides optimum noise reduction or noise suppression. The more acoustic dimensions there are in which the sound waves are propagated, the more difficult this problem becomes. In the space domain there will always be three acoustic dimensions.

By the use of active noise reduction based on destructive interference, the sound field which is required to be suppressed is detected by a special microphone arrangement, and after signal processing, the detected microphone signals are transmitted with the correct amplitude and phase to a loudspeaker which acts as the noise-cancelling sound source. In order that the noise cancellation should be effective, the sound which is detected by the microphone arrangement and the sound from the loudspeaker must be coherent, i.e. the distances between microphones, loudspeaker and the area in which the noise reduction or cancellation are to take place must be small. The problem is that small distances between microphone and loudspeaker which are connected in an electrical network will normally result in acoustic feedback, so-called howl.

For instance, U.S. Pat. No. 5,133,017 (Cain et al.) discloses a noise cancellation system providing a localized zone of noise suppression in the vicinity of, e.g., an individual person. This system uses a pair of loudspeakers—one for each ear—and a number of microphones to obtain a cancellation signal which is delivered to the loudspeakers. No distinction is made between the near field and the far field and the system does not address the problem of acoustic feedback.

Attempts have also been made to generate a local noise-suppressed area or a so-called quiet zone by using a reference signal. If, e.g., it is a case of noise from a rotating machine, which is common in cars and aircraft, the reference signal can be generated on the basis of the RPM of the rotating machine and the cancelling signal then generated on this basis. Thus the problem of feedback is avoided, but a system of this kind will only be capable of reducing noise which comes from the source of the reference signal and these sources should preferably be of such a nature that they limit a pure tone. This means that in practice this concept for active noise reduction is limited to noise from rotating machinery.

A further problem with active noise reduction in a local area is that the sound, i.e. the noise, is amplified in other areas. This will be a problem particularly in a noise reduction system which, e.g., is installed in a passenger seat, since noise reduction in one spot, i.e. in a passenger seat, can result in the noise being amplified in the area of the neighbouring seat.

The object of the present invention is to provide a method and a device for active noise reduction in a local area, whereby the above-mentioned problems are essentially eliminated.

This object is achieved with a method which is characterized by the features disclosed by claim 1 and a device which is characterized by the features disclosed by claim 9. Further features and advantages of the method and device according to the invention are disclosed by the dependent claims 2–8 and the dependent claims 10–14 respectively.

The method and the device according to the present invention will now be explained in more detail in connection with an example, whereby an embodiment of the device according to the invention illustrated in the accompanying drawing is used in order to implement the method according to the invention.

Figure 1:
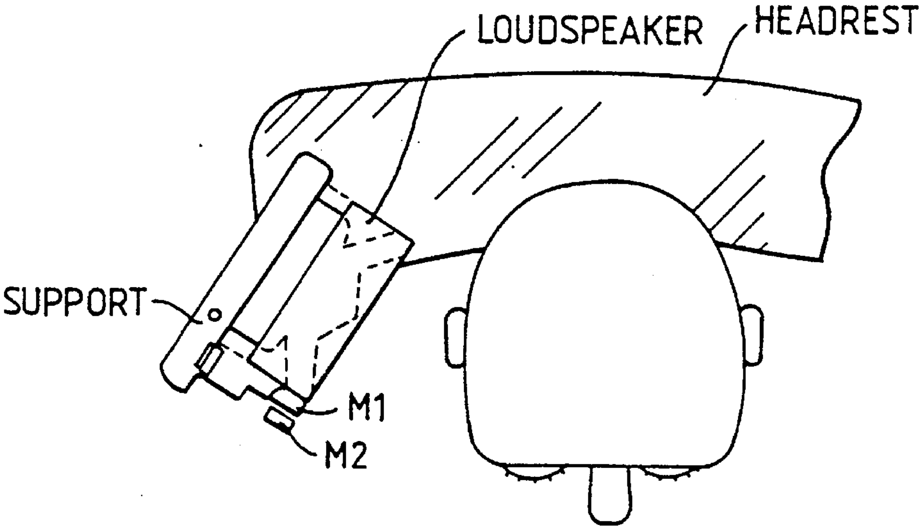
FIG. 1 is a schematic illustration of a technical installation for generating a quiet zone.

FIG. 1 illustrates an installation for generating a quiet zone, e.g. in connection with a seat which may be a driver's seat or a passenger seat in a vehicle or vessel. The installation comprises a loudspeaker which is preferably provided close to the head of the person using the seat. At the edge of the loudspeaker there are provided two microphones M1, M2 in the same plane, orthogonally on the loudspeaker's centre axis and in the same radial direction from this axis. However, the distance of the microphones M1, M2 from the loudspeaker's centre axis is somewhat different. The problem of acoustic feedback from the loudspeaker can thereby be eliminated by adjusting the mutual sensitivity and time delay between the microphones M1, M2 in such a way that sound from the loudspeaker is cancelled both with regard to direction and distance. The microphones M1, M2 have virtually the same sensitivity to sound from all the other parts of the enclosed space in which the installation is located, including in the direction of the loudspeaker, but beyond it. Thus an installation of this kind makes it possible to reduce sound from every point in the enclosed space in which the installation is employed.

As shown in FIG. 1, the microphones M1, M2 will pick up the sound, i.e. the noise or sound field in the enclosed space close to the location in which the noise reduction or cancellation is desired. Thus it will be possible in principle to generate automatically a correct cancellation independent of the sound field's volume and character in the time and frequency domains, the efficiency of the noise reduction in practice only being limited by the parameters determined by the system, such as the installation's geometry, the loudspeakers used, the microphones used and any electronic processing of those signals detected by the microphones.

The loudspeaker which is illustrated in FIG. 1 is an open loudspeaker, i.e. it has a so-called dipole characteristic, which means that the loudspeaker emits relatively little energy to the far field, but on the other hand generates a proportionately stronger near field. The loudspeaker is installed in such a manner that this near field will be located in the area where the noise requires to be cancelled. The installation will therefore avoid the problem of the sound being amplified in the area outside the cancellation zone. Furthermore it is also an advantage that an open loudspeaker with a dipole characteristic is used, since reduced feedback is obtained in the closed loop microphone-loudspeaker because the microphones M1, M2 are installed on the edge of the loudspeaker and preferably in the loudspeaker's front plane, as can be seen in FIG. 1.

The microphones M1, M2 which are used are omnidirectional microphones. The signals detected by the microphones M1, M2 are transmitted through respective microphone amplifiers and passed to first and second inputs on an analog/digital converter. The outputs from the analog/digital converter are connected with respective inputs on a digital signal processor, these inputs corresponding to the first and the second microphone signal respectively. The digital signal processor includes on the first microphone channel an attenuation stage and a delay stage attenuating and delaying the signal from the microphone which is located closest to the loudspeaker's centre axis. The same loudspeaker signals are thereby obtained in the two microphone channels. The processed microphone signal is then inverted in the digital signal processor in an inverter stage and the two microphone signals are then passed to a summation stage which adds them up. In the summation the loudspeaker noise which is picked up by the microphones M1, M2 is cancelled, while the microphones still detect the sound from all other parts of the enclosed space. This will lead to a considerable reduction in the acoustic feedback in the system and thereby improve the noise reduction in the quiet zone. Normally the two microphones M1, M2 will have a sensitivity disparity of approximately 10 dB. This means that sound which comes from all other directions and distances than from the loudspeaker will substantially be detected by the microphone which is located at the greatest distance from the loudspeaker's centre axis and thus the detection will in practice be omnidirectional.

The summed and processed digital microphone signal is supplied to a filter in the digital signal processor. This filter is preferably an FIR filter of the adaptive kind which is optimized in such a manner that the sound from the loudspeaker cancels the undesirable noise in an area which is located immediately in front of the loudspeaker, for example 10 cm from the loudspeaker.

It should be understood that the digital signal processor is implemented with software modules, attenuation, delay, inversion and summing preferably being performed in a first-software module, while the FIR filter constitutes a second software module.

The software modules will therefore correspond to equivalent electrical networks in a hypothetical analog signal processing.

Figure 2:
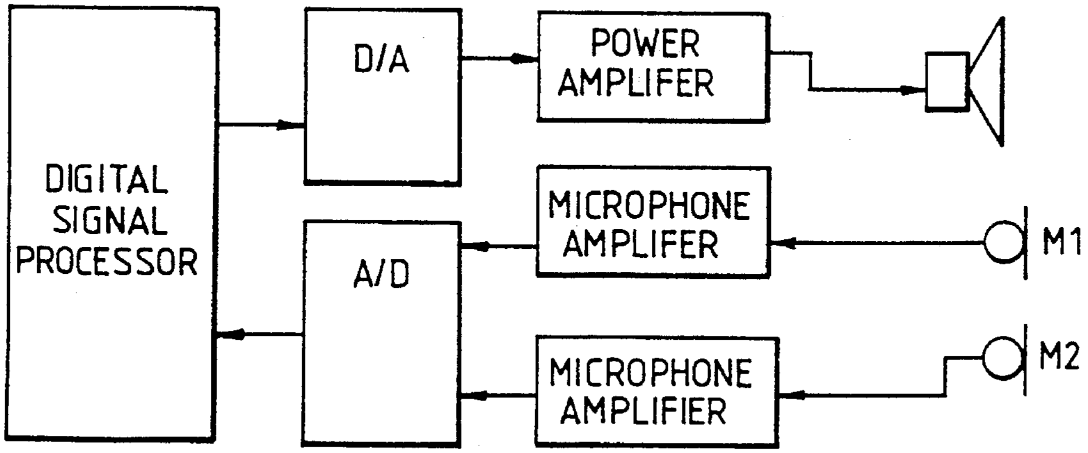
FIG. 2 is a block diagram for signal processing in generating a quiet zone.

As shown in, FIG. 2 a power amplifier is normally connected between the output of the digital/analog converter and the input to the loudspeaker, but the amplification could also be performed, e.g., on the digital output signal before conversion by implementing the digital/analog converter as a multiplying converter.

Thus the loudspeaker now obtains an input signal which represents the noise in the enclosed space, the loudspeaker's own output signal being eliminated. The actual output signal from the loudspeaker is given the correct amplitude and phase, i.e. the opposite phase of what can be regarded as the noise from the far field which enters the area in which noise reduction is desired. An efficient cancellation of the noise in this area is thereby achieved, thus creating a quiet zone, while at the same time the,feedback between loudspeaker and microphones is effectively reduced.

Experimental measurements using the method and the device according to the invention have shown that a reduction of 20.7 dB can be obtained in the acoustic feedback, and that the reduction in feedback is greatest at frequencies below 400 Hz. The margin of stability was found to be greater than 10 dB for all frequencies between 50 and 1000 Hz.

With a suitable adaptation of the FIR filter used, an integrated attenuation was achieved of up to 19.3 dB as measured at the ear of an artificial head used in the experimental investigation. The maximum attenuation was 31 dB and this was obtained at a frequency of 270 Hz, while the optimum attenuation band extended from 100 to 460 Hz. It was possible to obtain attenuation over a greater frequency range, but this reduced the integrated attenuation value. It was found that the filter's length of time and delay affected the possibility of attenuation. In the test arrangement used the FIR filter had to be able to simulate an impulse response with a duration of 10 ms in order to give an acceptable attenuation.

It should be understood that the method and the device employed for its implementation are not restricted to the embodiment illustrated here, but may in practice be implemented in other ways within the scope of the appended claims.

We claim:

1. A method for active noise reduction in a local area, especially for generating a so-called quiet zone in the local area, wherein a loudspeaker and two microphones are used, the meshed being characterized in that the loudspeaker is provided adjacent to the local area where the quiet zone is to be generated, the loudspeaker being an open loudspeaker, that a first microphone is provided at a given first radial distance from the loudspeaker's centre axis, that a second microphone is provided at a given second radial distance from the loudspeaker's centre axis, the second radial distance being greater than the first radial distance and the microphones being located in the same radial direction, orthogonal to the loudspeaker's centre axis, that the acoustic signal generated by the loudspeaker, overlaid on the sound field which exists in the local area, is detected with the first and the second microphone respectively, thus obtaining a first and second microphone signal respectively, that the first microphone signal is delayed by a value corresponding to the difference in running time between the first and second radial distance, that the first microphone signal is attenuated by a value corresponding to the difference in intensity between the detected microphone signals, thus obtaining a processed first microphone signal with the same intensity as the second microphone signal, whereafter the first processed microphone signal is inverted and summed with the second microphone signal to obtain a summed signal which, after filtering and amplification, is transmitted to the loudspeaker.

2. A method according to claim 1, characterized in that the two microphone signals are amplified after the output from the respective microphone, but before processing.

3. A method according to claim 2, characterized in that the amplified microphone signals before processing are converted to digital signals in an analog/digital converter.

4. A method according to claim 3, characterized in that the digital signals are processed in a digital signal processor, the first digital signal which corresponds to the first microphone signal being attenuated, delayed and inverted before being summed with the second digital signal which corresponds to the second microphone signal, whereafter the summed digital signal is filtered and converted to an analog output signal in a digital/analog converter, and amplified in a power amplifier and transmitted to the loudspeaker.

5. A method according to claim 4, characterized in the that for the filtering an FIR filter is used.

6. A method according to claim 1 characterized in the use of microphones with omnidirectional characteristic.

7. A method according to claim 1 characterized in the use of a loudspeaker with dipole characteristic.

8. A method according to claim 1 characterized in that optimum noise reduction is obtained in the space domain or the frequency domain through an adaptation of the filter.

9. A device for active noise reduction in a local area, especially for generating a so-called quiet zone in the local area, comprising a loudspeaker and two microphones, characterized in that the loudspeaker is provided adjacent to the local area in which the quiet zone is to be generated, the loudspeaker being an open loudspeaker, that there is provided a first microphone (M1) at a given first radial distance from the loudspeaker's centre axis, that there is provided a second microphone (M2) close to the first at a given second and greater radial distance from the loudspeaker's centre axis, the microphones (M1, M2) being located in the same radial direction, orthogonal to the loudspeaker's centre axis, that the output from each of the microphones (M1, M2) is connected with respective inputs on an analog/digital converter, that the outputs on the analog/digital converter are connected with respective inputs on a digital signal processor, each input corresponding to a microphone channel, that the signal processor includes an attenuation stage connected to the input which corresponds to the first microphone channel, a delay stage connected to the output on the attenuation stage and an inverter stage connected to the output on the delay stage, that the output on the inverter stage is led to a first input on a summation stage whose second input is connected with the second microphone signal channel, that the output on the summation stage is connected with a filter stage connected in front of the output on the digital signal processor, and that the output on the digital signal processor is connected via a digital/analog converter with the input on a loudspeaker.

10. A device according to claim 9, characterized in the loudspeaker having a dipole characteristic.

11. A device according to claim 10, characterized in the microphones having omnidirectional characteristic.

12. A device according to claim 8 characterized in that between each microphone and the input on the analog/digital converter there is connected a microphone amplifier.

13. A device according to claim 8, characterized in that the filter in the digital signal processor is an FIR filter, preferably an adaptive FIR filter.

14. A device according to claim 8, characterized in that between the digital/analog converter and the loudspeaker there is connected a power amplifier.

* * * * *